United States Patent [19]

Jones et al.

[11] 4,419,368

[45] Dec. 6, 1983

[54] NAPHTHOQUINONE ANTI-PSORIATIC AGENTS

[75] Inventors: Gordon H. Jones, Cupertino; John Young, Redwood City, both of Calif.

[73] Assignee: Syntex (U.S.A.) Inc., Palo Alto, Calif.

[21] Appl. No.: 317,645

[22] Filed: Nov. 2, 1981

Related U.S. Application Data

[60] Continuation-in-part of Ser. No. 144,479, Apr. 28, 1980, abandoned, which is a division of Ser. No. 912,697, Jun. 5, 1978, Pat. No. 4,229,478.

[51] Int. Cl.$^3$ .............................................. A61K 31/12
[52] U.S. Cl. ................................. 424/331; 260/396 R; 424/251; 424/263; 424/273 R; 424/304; 424/308
[58] Field of Search .................. 424/331, 263, 304; 260/396 R

[56] References Cited

U.S. PATENT DOCUMENTS 3,914,264 10/1975 Marsico et al. ................. 260/396 R
4,229,478 10/1980 Jones et al. .......................... 424/331

FOREIGN PATENT DOCUMENTS 1243401 8/1971 United Kingdom .
1243402 8/1971 United Kingdom .

*Primary Examiner*—Leonard Schenkman
*Attorney, Agent, or Firm*—Annette M. Moore; Tom M. Moran

[57] ABSTRACT

Psoriasis in mammals is relieved by topically administering substituted naphthoquinone of the formula:

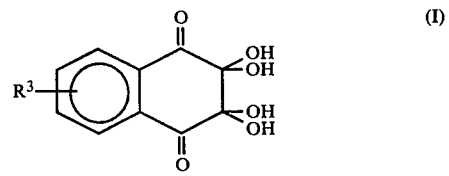

wherein:

$R^3$ is halo, linear or branched alkoxy of one to eighteen carbon atoms or —S(O)$_n$R wherein:

n is 0, 1 or 2; and

R is a alkyl of one to eighteen carbon atoms, alkoxycarbonylalkyl, optionally substituted phenyl, optionally substituted phenylalkyl or optionally substituted heterocyclic aryl and the pharmaceutically acceptable salts of said heterocyclic aryl.

10 Claims, No Drawings

NAPHTHOQUINONE ANTI-PSORIATIC AGENTS

This is a continuation-in-part of U.S. Ser. No. 144,479 now abandoned filed on Apr. 28, 1980 which is a division of U.S. Ser. No. 912,697, filed June 5, 1978 now U.S. Pat. No. 4,229,478.

BACKGROUND OF THE INVENTION

1. Field of the Invention

The invention relates to pharmaceutical compositions which are useful in inhibiting certain dermatological conditions. More particularly, this invention relates to pharmaceutical compositions and methods useful in relieving the effects of certain chronic recurrent papulosquamous dermatoses, e.g., psoriasis.

2. Related Disclosures

Psoriasis is a skin disease characterized in part by excessive proliferation of cells of the epidermis which remain strongly adherent and build up into a scaley plaque typical of the disease. Currently available therapies, which are not curative, depend on the control of epidermal cell proliferation through the use of hormonal agents, such as corticosteroids or through the use of compounds related to cancer chemotherapy such as hydroxyurea, methotrexate, and the nitrogen mustards.

While the above agents are effective to a certain extent, they cause numerous severe undesirable side effects including renal irritation and erythema.

Unsubstituted 2,2,3,3-tetrahydroxy-1,2,3,4-tetrahydro-1,4-naphthoquinone and its uses in treating psoriasis are known. See British Pat. Nos. 1,243,401 and 1,243,402. See also Khim.-Farm. Zh. 1970, 4(11), 56-8.

SUMMARY

The present invention provides a pharmaceutical composition in a form suitable for topical administration to mammals comprising a psoriasis-relieving amount of a compound of the formula:

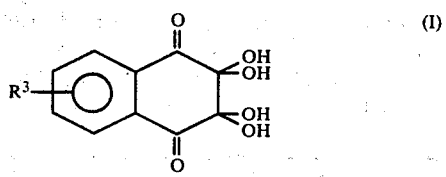

together with at least one pharmaceutically acceptable carrier wherein $R^3$ is selected from the group halo, cyano, alkoxy and —S(O)$_n$R wherein n is 0, 1 or 2;

R is selected from the group alkoxycarbonylalkyl; alkyl; phenylalkyl wherein the phenyl ring is optionally substituted by one or more lower alkyl, lower alkoxy, halo or lower acyl; phenyl optionally substituted by one or more halo, cyano, nitro, amino, acylamino, lower alkoxy or lower alkyl; and heterocyclic aryl or the pharmaceutically acceptable salts thereof, said aryl having 3 to 9 ring carbon atoms and having in the ring one or two heteroatoms selected from the group consisting of nitrogen, oxygen and sulfur, said heterocyclic aryl being optionally substituted by one or more halo, cyano, lower alkyl or lower alkoxy.

Another aspect of the invention is a method for relieving the condition of psoriasis in a mammal which comprises topically administering to said mammal a psoriasis-relieving amount of a compound of formula (I).

DETAILED DESCRIPTION AND PREFERRED EMBODIMENT

In its broadest aspect, the present invention provides a pharmaceutical composition in a form suitable for topical administration to mammals comprising a psoriasis-relieving amount of a compound of the formula:

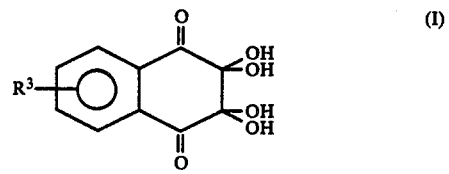

together with at least one pharmaceutically acceptable carrier wherein $R^3$ is selected from the group halo, cyano, alkoxy and —S(O)$_n$R wherein n is 0, 1 or 2;

R is selected from the group alkoxycarbonylalkyl; alkyl; phenylalkyl wherein the phenyl ring is optionally substituted by one or more lower alkyl, lower alkoxy, halo or lower acyl; phenyl optionally substituted by one or more halo, cyano, nitro, amino, acylamino, lower alkoxy or lower alkyl; and heterocyclic aryl or the pharmaceutically acceptable salt thereof, said aryl having 3 to 9 ring carbon atoms and having in the ring one or two heteroatoms selected from the group consisting of nitrogen, oxygen and sulfur, said heterocyclic aryl being optionally substituted by one or more halo, cyano, lower alkyl or lower alkoxy.

More specifically, the present invention provides a pharmaceutical composition in a form suitable for topical administration to mammals containing a compound of formula (I) and a pharmaceutically acceptable, non-toxic carrier wherein $R^3$ is substituted at the 5- or 6-position of the naphthoquinone ring.

An even more specific embodiment of the instant invention is a pharmaceutical composition as described hereinabove wherein $R^3$ is bromo, chloro, fluoro, cyano, phenylthio, methylthio, methoxy, ethoxy, n-propoxy, isopropoxy, n-butoxy, and sec-butoxy.

Particularly preferred are pharmaceutical compositions in a form suitable for topical administration to mammals containing a pharmaceutically acceptable non-toxic carrier and one or more of a psoriasis-relieving amount of the following compounds:

6-chloro-2,2,3,3-tetrahydroxy-1,2,3,4-tetrahydro-1,4-naphthoquinone;

6-fluoro-2,2,3,3-tetrahydroxy-1,2,3,4-tetrahydro-1,4-naphthoquinone;

6-bromo-2,2,3,3-tetrahydroxy-1,2,3,4-tetrahydro-1,4-naphthoquinone;

6-methoxy-2,2,3,3-tetrahydroxy-1,2,3,4-tetrahydro-1,4-naphthoquinone;

5-chloro-2,2,3,3-tetrahydroxy-1,2,3,4-tetrahydro-1,4-naphthoquinone;

5-phenylthio-2,2,3,3-tetrahydroxy-1,2,3,4-tetrahydro-1,4-naphthoquinone; and 5-methylthio-2,2,3,3-tetrahydroxy-1,2,3,4-tetrahydro-1,4-naphthoquinone.

In the present specification and claims the term "alkyl" is intended to mean alkyl groups containing one to eighteen carbon atoms including straight chain groups, or branched chain groups. Illustrative of such groups are for example, methyl, ethyl, n-propyl, isopropyl, n-hexyl, 2-methylpentyl, n-octyl, n-dodecyl and n-octadecyl. The term "lower alkyl" refers to alkyl groups of one to four carbon atoms. Examples of "lower alkyl" groups are methyl, ethyl, n-propyl, i-propyl, n-butyl, i-butyl, s-butyl and t-butyl. The term "phenylalkyl" refers to an optionally substituted phenyl ring attached to an alkylene chain of one to eighteen carbon atoms. Examples of "phenylalkyl" are benzyl, 4-methylbenzyl, 4-chlorobenzyl, phenylbutyl, phenyldodecyl, 4-chlorophenyloctadecyl and the like.

The term "lower acyl" refers to the group RC(O)— wherein R is an alkyl group of one to six carbon atoms or a phenyl group. Examples of "lower acyl" are acetyl, propionyl, butyryl and benzoyl. The term "alkoxycarbonylalkyl" refers to an ester group of the formula ROC(O)— substituted on an alkyl group wherein R and alkyl is as defined above. Examples of "alkoxycarbonylalkyl" are methoxycarbonylmethyl, ethoxycarbonylmethyl, ethoxycarbonylethyl, propoxycarbonylethyl and the like.

The term "alkoxy" is intended to mean the straight or branched aliphatic groups of one to eighteen carbon atoms having bonded thereto an oxygen moiety. Examples of "alkoxy" include methoxy, ethoxy, n-hexyloxy, n-octyloxy and n-octadecoxy. The term "lower alkoxy" refers to a straight or branched chain aliphatic group of one to four carbon atoms having bonded thereto an oxygen moiety. Examples of "lower alkoxy" are methoxy, ethoxy, n-propoxy, i-propoxy, n-butoxy, i-butoxy, s-butoxy and t-butoxy. The term "phenylalkoxy" refers to an optionally substituted phenyl ring attached to an alkoxy group of one to eighteen carbon atoms as defined above. Examples of "phenylalkoxy" are benzoxy, 4-chlorophenyl-n-butoxy, 4-methylphenyl-n-hexyloxy and the like.

The term "halo" refers to fluoro, chloro, and bromo. The term "acylamino" refers to the group $R^4C(O)NR^5$ wherein $R^4$ and $R^5$ are independently hydrogen or lower alkyl as defined above. Examples of "acylamino" are carbamoyl, acetylamino, propionylamino and n-butyrylamino. The term "cyano" refers to the group —CN. The term "amino" refers to the group —$NH_2$. The term "heterocyclic aryl" is defined as those cyclic aromatic compounds having 3 to 9 ring carbon atoms and having one or two heteroatoms in the ring selected from the group nitrogen, oxygen and sulfur. Examples of such include the groups thiopyranyl, benzothiopyranyl, furyl, 2H-pyryl, pyrroyl, imidazolyl, pyrazolyl, pyridinyl, pyrimidinyl, indolyl, quinolinyl, indazolyl and the like. These heterocyclic aryls may be optionally substituted with halo, lower alkyl, cyano and lower alkoxy.

By the term "pharmaceutically acceptable salts" as used in the case of the various $R^3$ containing heterocyclic aryl substituents herein is intended to mean those non-toxic pharmaceutically acceptable hydrogen-anion addition salts which do not adversely affect the pharmaceutical properties of the parent compounds. With respect to these addition salts, suitable inorganic anions include, for example, chloride, bromide, iodide, sulfate, phosphate, nitrate, and the like. Suitable organic anions include, for example, acetate, benzoate, lactate, picrate, propionate, butyrate, valerate, tartrate, maleate, fumarate, citrate, succinate, tosylate, ascorbate, nicotinate, adipate, gluconate and the like.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthoquinones of formula (I) may be formulated with suitable pharmaceutical vehicles known in the art to form particularly effective topical compositions. An effective amount of the naphthoquinone is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthoquinones therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50–99 parts by weight |
| Fatty Alcohol | 1–20 |
| Non-ionic Surfactant | 0–10 |
| Mineral Oil | 0–10 |
| Typical Pharmaceutical Adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The naphthoquinones of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White Petrolatum | 40-94 parts by weight |
| Mineral Oil | 5-20 |
| Glycol Solvent | 1-15 |
| Surfactant | 0-10 |
| Stabilizer | 0-10 |
| Active Ingredients | 0.001-10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001-10.0 parts by weight |
| Propylene Carbonate | 1-10 |
| Solvent | 1-10 |
| Surfactant | 0-10 |
| White Petrolatum | 70-97 |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

| | |
|---|---|
| Glycol Solvent | 40-35 parts by weight |
| Fatty Alcohol | 15-45 |
| Compatible Plasticizer | 0-15 |
| Compatible Coupling Agent | 0-15 |
| Penetrant | 0-20 |
| Active Ingredients | 0.001-10.0 |

Another aspect of the invention is a method for relieving the condition of psoriasis in a mammal by topically administering a composition containing a compound of formula (I) wherein $R_3$, n and R are as defined above. Generally, the anti-psoriatic manifestation in mammals, particularly humans, is combatted by contacting the inflamed areas with a therapeutically effective amount of the naphthoquinone-containing compositions of this invention, that is, an amount which results in a lessening of the epidermal cell proliferation (an anti-psoriatic effect). Preferably the naphthoquinones are first formulated to prepare a suitable pharmaceutical formulation, as discussed hereinabove, which is then placed in contact with the afflicted area(s). An effective amount of the naphthoquinone will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

PREPARATION

The compounds of the instant invention may be prepared from the 2,3-dihydroxy or 2,3-dialkoxy-substituted-1,4-naphthoquinone.

The intermediate 2,3-dihydroxy or 2,3-dialkoxy-substituted-1,4-naphthoquinones may be prepared by the following reaction sequence:

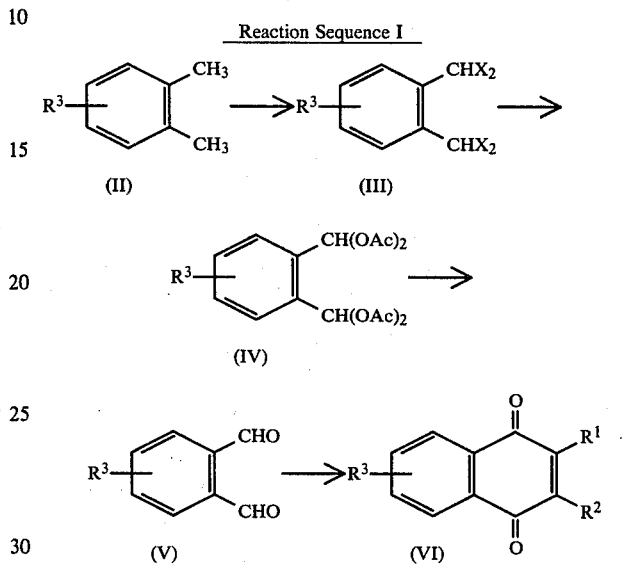

wherein $R^1$ and $R^2$ are independently hydroxy or alkoxy and X is chloro, bromo or iodo. This process is preferred when $R^3$ is in the 6 position.

Initially, the methyl groups of the $R^3$ substituted ortho-xylene, compounds of formula (II) are directly halogenated. Disubstitution of halo on each of these groups is found to be most facile when bromo is the desired halo substituent. The reaction occurs readily using N-bromosuccinimide as the brominating agent. See for example, Djerassi, Chem. Revs., 43, 271 (1948). Compounds of formula (III), the $\alpha,\alpha,\alpha',\alpha'$-tetrabromoortho-xylene, is next dehalogenated in a manner known for the hydrolysis of gem-dihalides in the presence of a suitable catalyst. The catalysts include, for example, calcium carbonate, sulfuric acid, morpholine and various silver salts. Typically, a mixture of acetic acid, compounds of formula (III) and silver acetate is heated, forming compounds of formula (IV) which are readily converted to compounds of formula (V) typically with base such as sodium bicarbonate. The $R^6$-substituted-1,2-phthalaldehyde intermediate is next converted to the $R^6$-substituted-2,3-dihydroxy-1,4-naphthoquinone, compounds of formula (VI) where $R^1=R^2=OH$, by reaction with glyoxal. This reaction is reported in some detail in German Patent No. 859,008. It is sometimes more convenient to prepare the above disclosed $R^3$-substituted-1,2-phthalaldehyde compounds of formula (III) directly from compounds of formula (II), by the classical Etard oxidation. See for example Hartford et al, Chem. Revs., 58, 1 (1958). This oxidation is readily effected with chromyl chloride.

The compounds of formula (VI) bearing the 6- or the 5-substituent, particularly the 5-substituent may also be prepared from compounds of formula (X).

The intermediates of formula (X) may be prepared by the reaction sequence below.

Reaction Sequence II

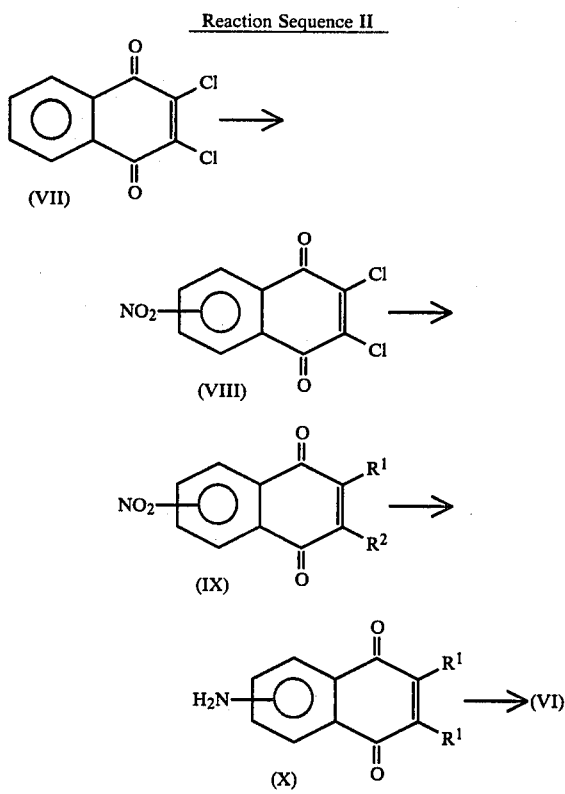

wherein $R^1 = R^2 =$ alkoxy.

Compounds of formula (X) are prepared by starting with a 2,3-dihalonaphthoquinone, preferably 2,3-dichloro-1,4-naphthoquinone, compound of formula (VII), and directly nitrating. The reaction proceeds in the manner known for polycyclic aromatic compounds to yield a mixture of the 5- and 6-nitro-2,3-dichloro-1,4-naphthoquinones, compounds of formula (VIII). The reaction is conducted typically with concentrated nitric acid in a low pH solvent medium, preferably concentrated sulfuric acid, typically at 20° to 100° for a time sufficient to complete the reaction. Depending on the reaction temperature and times of reaction, ratios of the 5-nitro isomer:6-nitro isomer mixture may range from 10:1 to 1:10, typically 8:1.

Compounds of formula (IX) where $R^1 = R^2 =$ alkoxy are synthesized from 5- and 6-nitro-2,3-dichloro-1,4-naphthoquinone, compound of formula (VIII), by condensing them with an alkali metal alkoxide, wherein the alkoxide moiety is $R^1 = R^2$. The reaction is preferably conducted in an inert organic solvent such as tetrahydrofuran, dimethylsulfoxide, dimethylformamide and the like at temperatures from about 20° to about 100° for a time sufficient to assure completeness of reaction, i.e., for about 2 hours to about 48 hours.

The compounds of formula (X) are prepared from compounds of formula (IX) by catalytic or noncatalytic reduction processes known in the prior art. Metal-acid reducing agent compositions, such as granulated iron and hydrochloric acid, tin and hydrochloric acid, and the like or neutral reducing agent compositions such as zinc dust and aqueous alcohol or aluminum amalgam and aqueous alcohol as well as organo-metallic reducing agents such as lithium aluminum hydride, sodium borohydride and the like may be used in this reduction. Preferably, the reduction is accomplished by treating the compounds of formula (IX) with excess hydrazine in the presence of a catalytically sufficient amount of palladium, typically on carbon. The reaction readily occurs at room temperature, the time of reaction being governed by the rate of addition of the hydrazine to the reaction mixture such typically being about 1 to about 10 hours.

Compounds of formula (X) are converted into compounds of formula (VI) where $R^3$ is halo by adding to the compound of formula (X) in an acidified aqueous solution, a solution of an alkali metal nitrite. This initial reaction forms the diazonium salt at the 5- or 6-position of the naphthoquinone ring. The salt is decomposed with a solution of cuprous halide dispersed or dissolved in the corresponding halogen acid (the Sandmeyer reaction). This classical reaction is treated extensively in Bigelow, Org. Synthesis, Coll. Vol. I, 126–133 (1941).

A modification of the above Sandmeyer reaction is useful in the preparation of the compounds of formula (VI) where $R^3$ is cyano in that the diazonium salt, rather than being decomposed in the presence of cuprous halide/halogen acid is decomposed in the presence of an alkali metal cyanide and a cuprous halide. See Clarke and Read, Org. Synthesis, Coll. Vol. I, 514 (1941) for a further explanation of the considerations involved in this modified Sandmeyer reaction.

The compounds of formula (VI) where $R^3$ is an optionally substituted heterocyclic aryl thio group, optionally substituted phenylthio or alkylthio may also be prepared from the diazonium salt (above). For example, the diazonium salt of the compound of formula (X) is reacted with an alkali solution of thiophenol to yield the compounds of formula (VI) where $R^3$ is 5-phenylthio. Typically, the displacement reaction of the diazonium salt is carried out at 30°–75° by adding an alkali solution of thiophenol in an inert organic solvent. Solvents of preference are the inert solvents such as ethyl acetate, tetrahydrofuran and the like. Reaction times may vary from 10 minutes to about 24 hours.

The 5-heterocyclic arylthio compounds are preferably prepared by adding the 2,3-dialkoxy-5-nitro-1,4-naphthoquinone of formula (IX) to a solution of the thiol-substituted heterocyclic aryl compound admixed with an alkali metal hydride in an inert organic solvent such as dimethylformamide. The reaction is typically conducted at −75° to −25° C. over a period of about 10 to about 60 minutes.

The preferred procedure for the preparation of the compounds of formula (VI) where $R^3$ is a linear or branched alkylthio or an optionally substituted phenylalkylthio is by first converting a compound of formula (X) to the di(2,3-$R^1$,$R^2$-1,4-naphthoquinone)-5-disulfide of the following formula:

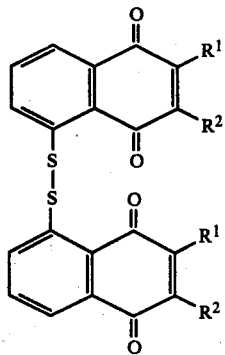

(XI)

wherein $R^1=R^2=$alkoxy. A mixture of an alkaline earth or alkali metal thiol carboxylate such as the acetate, propionate, butyrate and the like (compounds of the formula

$$M(OC(CH_2)_ySH)_x$$

where y is the integer 0 to 18, M is an alkali or alkaline earth metal and x is the valence of said metal) in an inert organic solvent is added to a solution or dispersion of compound of formula (X) at a temperature of $-10°$ to $+10°$ C. over a period of about 1 to about 120 minutes, preferably 5 to 30 minutes. Reaction media include a variety of polar inert solvents such as dimethylformamide dimethylsulfoxide and the like. After further reaction, typically for about 1 to about 10 hours at 20° to 50°, the disulfide is isolated. This compound can then be used to prepare the alkyl or aralkyl sulfides of formula (VI) by first treating the disulfide with a mixture of sodium borohydride in an inert organic solvent and adding to such mixture at a temperature of about $-10°$ to about 75° for 1 to 10 hours an appropriate alkylating agent such as a dialkyl sulfate, an alkyl halide, an aralkyl halide and the like. Illustrative of such alkylating agents are the compounds methyl bromide, methyl iodide, dimethyl sulfate and benzyl bromide. Preferably alkyl iodide is used as the alkylating agent herein.

The sulfinylnaphthoquinones of formula (VI) are prepared by oxidation of the corresponding thio compounds with a suitable peracid in an inert organic solvent.

The compounds of formula (VI) bearing a 5-sulfonyl substituent are prepared by further oxidizing the compounds of formula (VI) wherein $R^3$ is a sulfinyl group with a suitable peracid typically at $-10°$ to 75° for 1 to 10 hours. Preferably, m-chloroperbenzoic acid in an inert organic solvent at room temperature is used to prepare the desired sulfonyl compounds.

Where appropriate, salts of the compounds bearing heterocyclic aryl substituents are prepared. For example, the methylsulfate salt of the 2,3-dialkoxy-5-(pyridin-4-ylthio)-1,4-naphthoquinone is readily prepared by admixture with dimethylsulfate in an inert organic solvent such as tetrahydrofuran. Salt formations of this type are well known in the prior art.

The above preparations are generally carried out starting with various 5- or 6-substituted 2,3-dialkoxy-1,4-naphthoquinones, compounds of formula (VI) where $R^1=R^2=$linear or branched alkoxy. These alkoxy groups are readily hydrolyzed to yield the 2,3-hydroxy compounds. The reaction is preferably carried out at $-10°$ to 70° for 1 to 10 hours in an inert organic solvent such as methylene chloride having added thereto a freshly distilled solution of boron trichloride.

The compounds of the present invention of formula (I) are prepared by treating a compound of formula (VI) wherein $R^1$ and $R^2$ are hydroxy or alkoxy and $R^3$ is as previously defined with a mixture of chlorine in acetic acid which undergoes facile oxidation to produce optionally 5- or 6-substituted-2,2,3,3-tetrahydroxy-1,2,3,4-tetrahydro-1,4-naphthoquinone, the compounds of formula (I). The reaction is typically carried out by passing chlorine gas through a 50% aqueous acetic acid solution of compounds of formula (VI) at about 10° to about 100°, preferably 20° to 40° for a time sufficient to complete the reaction, typically 0.5 to 48 hours, and isolating the compounds of formula (I) by cooling the final reaction solution. The procedure is disclosed in detail in British Pat. No. 1,243,402. Other effective oxidizing agents include alkali metal persulfates, hydrogen peroxide, sodium peroxide, bromine in acetic acid and the like. Temperatures and times of reaction for these other oxidizing agents are well known by those skilled in the art.

The following specific description is given to enable those skilled in the art to more clearly understand and practice the present invention. It should not be considered as a limitation upon the scope of the invention but merely as illustrative and representative thereof.

All temperatures in this specification are in degrees Centigrade unless otherwise noted.

PREPARATION 1

4-Chloro-α,α,α', α'-tetrabromo-o-xylene (Compounds of formula (III) where $R^3$ is at the 4-position.)

A mixture of 4-chloro-o-xylene (14.0 g, 0.1 mol) and freshly recrystallized N-bromosuccinimide (80 g, 0.45 mol) in carbon tetrachloride (1 L) is irradiated for 2½ hours (hr) with a 250 watt tungsten infrared lamp positioned so that the solvent refluxed gently. The solid material is then removed by filtration, the filtrate is concentrated in vacuo and the crystalline residue is recrystallized from isopropanol giving 34 g of α,α,α',α'-tetrabromo-1-xylene, mp 108°-111° [Bull. Soc. Chim., 2966 (1966), mp 114°].

In a similar fashion, the following compounds are prepared:

4-fluoro-α,α,α',α'-tetrabromo-o-xylene, mp 87°-91°;
4-bromo-α,α,α',α'-tetrabromo-o-xylene, mp 102°-105° (lit. 116°);
4-methoxy-α,α,α',α'-tetrabromo-o-xylene, bp 160° (bath temp.), 0.1 mm; and
4-cyano-α,α,α',α'-tetrabromo-o-xylene, mp 114°-115°.

PREPARATION 2

4-Chloro-1,2-phthalaldehyde (Compounds of formula (V))

A mixture of 4-chloro-α,α,α',α'-tetrabromo-o-xylene (22.8 g, 0.05 mol), silver acetate (36.6 g, 0.22 mol) and glacial acetic acid (500 ml) is heated under reflux for 1½ hr. The silver salts are filtered off, washed with chloroform and the combined filtrates concentrated to dryness in vacuo. The last traces of acetic acid are removed from the residue by evaporation with toluene. The resultant semicrystalline 4-chloro-1,2-bis(diacetyloxymethylene)benzene is dissolved in dioxane (500 ml) and a solution of sodium carbonate (53 g) in water (500 ml) is added. This mixture is shaken vigorously at 22° for 20 minutes, saturated with sodium chloride and then extracted with ethyl acetate (2×500 ml). The combined organic extracts are washed with brine (2×400 ml), dried with MgSO$_4$ and concentrated in vacuo giving 6.0 g of almost pure 4-chloro-1,2-phthalaldehyde. Sublimation at 75° and 0.05 mm Hg affords 5.4 g of 4-chloro-1,2-phthalaldehyde, mp 72°–76°.

In a similar manner, the following compounds are prepared:
4-fluoro-1,2-phthalaldehyde, mp 37°–40°;
4-bromo-1,2-phthalaldehyde, mp 87°–94°;
4-methoxy-1,2-phthalaldehyde, mp 44°–45°; and
4-cyano-1,2-phthaladehyde, mp 127°–128°.

PREPARATION 3

6-Chloro-2,3-dihydroxy-1,4-naphthoquinone (Compounds of formula (VI) where $R^3$ is chloro and $R^1=R^2=OH$.)

A solution of sodium carbonate (12.3 g) in water (290 ml) is added to a vigorously stirred solution of 4-chloro-1,2-phthalaldehyde (4.88 g, 29 mmol) in an oxygen atmosphere followed immediately by the addition, over a five minute period, of a solution of glyoxal bisulfite (16.4 g, 58 mmol) and potassium cyanide (1.88 g, 29 mmol) in water (290 ml). The reaction mixture is stirred in the oxygen atmosphere for a further 5 minutes. It is then treated with 6 N hydrochloric acid (50 ml), cooled in an ice-salt bath and further diluted with water (500 ml). The crystalline product is collected by filtration, washed with water, dried and recrystallized from water:methanol (2:1) giving 3.56 g of 6-chloro-2,3-dihydroxy-1,4-naphthoquinone, mp 228°–229°.

Anal. Calcd. for $C_{10}H_5ClO_4$ (224.60): C, 53.48; H, 2.24. Found: C, 53.50; H, 2.30.

In a similar manner the following compounds are prepared:
6-fluoro-2,3-dihydroxy-1,4-naphthoquinone, mp 217°–218°;
6-chloro-2,3-dihydroxy-1,4-naphthoquinone, mp 240°–241° [lit., Berichte, 80, 391, 397 (1947), mp 240°–241°];
6-methoxy-2,3-dihydroxy-1,4-naphthoquinone, mp 224°–225°; and
6-cyano-2,3-dihydroxy-1,4-naphthoquinone, mp 315°–320°.

PREPARATION 4

2,3-Dichloro-5- and 6-nitro-1,4-naphthoquinone (Preparation of Compounds of Formula (VIII))

Finely powdered 2,3-dichloro-1,4-naphthoquinone 50 g. 0.22 mol) is added to a stirred mixture of concentrated sulfuric acid (170 ml) and 90% nitric acid (102 ml) at a rate so that the exothermic reaction raises the temperature to 60°. The resulting mixture is stirred at 60° for a further 2 hours. The yellow crystalline solid is filtered off, washed thoroughly with water and recrystallized from chloroform giving 22.9 g of the 5-nitro isomer, mp 156°–157°. The above strongly acidic filtrate is poured onto ice water. The resultant solid is filtered off, washed thoroughly with water and dried giving 20.8 g of a mixture of the 5- and 6-isomer. Fractional crystallization of this mixture from acetic acid and chloroform:isopropanol affords 2.8 g of the 6-nitro isomer, mp 184°–187°.

Further quantities of both 5- and 6-isomer are obtained from the recrystallization mother liquors by chromatography on a silica gel column eluting with chloroform:cyclohexane mixtures.

PREPARATION 5

2,3-Dimethoxy-5-nitro-1,4-naphthoquinone (Preparation of Compounds of Formula (IX))

A solution of 2,3-dichloro-5-nitro-1,4-naphthoquinone (2.72 g, 10 mmol) in anhydrous tetrahydrofuran (15 ml) is added to a solution of 1 N sodium methoxide (25 ml, 25 mmol) and the resulting solution stored at 22° for 16 hours. Acetic acid (1 ml) is then added, the solution concentrated in vacuo and the residue partitioned between water (50 ml) and chloroform (100 ml). The aqueous phase is further extracted with chloroform (2×50 ml). The combined chloroform extracts are dried with MgSO$_4$ and concentrated in vacuo. The residue is recrystallized from methanol giving 1.99 g of 2,3-dimethoxy-5-nitro-1,4-naphthoquinone, mp 156°–157°.

In the same fashion the following compounds are prepared:
2,3-dimethoxy-6-nitro-1,4-naphthoquinone, mp 113°–114°; and
2,3-dibenzyloxy-5-nitro-1,4-naphthoquinone, mp 116°–117° (from sodium benzyloxide).

PREPARATION 6

2,3-Dimethoxy-5-amino-1,4-naphthoquinone (Preparation of Compounds of Formula (X))

Hydrazine (4.0 ml, 125 mmol of 97%) is added dropwise, over a 2 hour period, to a stirred mixture of the captioned compound of Preparation 5 (19.9 g, 75.6 mmol), 5% palladium on carbon (10 g) and ethanol (750 ml) in a nitrogen atmosphere. The catalyst is filtered off through a celite pad that was washed with hot ethanol (2×300 ml). The combined filtrate and washings are concentrated to dryness in vacuo and the residue recrystallized from water:ethanol (1.5:1) giving 14.6 g of 2,3-dimethoxy-5-amino-1,4-naphthoquinone, mp 116°–117°.

Similarly, 2,3-dimethoxy-6-amino-1,4-naphthoquinone, mp 196°–197° C., is prepared.

PREPARATION 7

5-Chloro-2,3-dimethoxy-1,4-naphthoquinone (Preparation of Compounds of Formula (VI) where $R^3$ is chloro)

A solution of sodium nitrite (0.69 g, 10 mmol) in water (5 ml) is added at 0°–5° to a solution of 5-amino-2,3-dihydroxy-1,4-naphthoquinone (1.17 g, 5 mmol) in 5:1 acetic acid:water (25 ml) containing concentrated hydrochloric acid (1.7 ml). A further quantity of sodium nitrite (0.69 g) is then added to the reaction mixture after cooling to −5°, followed by a solution of cuprous chloride (0.6 g) in concentrated hydrochloric acid (5 ml). The mixture is allowed to warm to 22° and solid cuprous chloride is added portionwise until the mixture assumes a green color. Water is then added to the reaction mixture and the precipitated yellow solid filtered off, washed with water and recrystallized from methanol:water (2:1) giving 1.01 g of 5-chloro-2,3-dimethoxy-1,4-naphthoquinone, mp 120°-121°.

PREPARATION 8

5-Cyano-2,3-dimethoxy-1,4-naphthoquinone (Preparation of Compounds of Formula (VI) where $R^3$ is cyano)

A solution of sodium nitrite (2.21 g, 32 mmol) in water (6 ml) is added at 0°-5° to a stirred suspension of 5-amino-2,3-dimethoxy-1,4-naphthoquinone (3.73 g, 16 mmol) in 3:1 water:tetrahydrofuran (20 ml) containing concentrated hydrochloric acid (6.7 ml) and the resulting mixture is stirred at 0°-5° for a further 1¼ hour. The almost clear solution is then neutralized with sodium carbonate, filtered and added at 5° to a vigorously stirred solution of cuprous chloride (4.75 g) and sodium cyanide (5.88 g) in water (80 ml). Ethyl acetate (100 ml) is added and the mixture is heated at 45° for 0.5 hours, filtered through a celite bed and separated into the two phases. The aqueous phase is extracted with ethyl acetate (2×100 ml). The combined organic phases are extracted with brine (150 ml), dried over MgSO₄ and concentrated to dryness in vacuo. The residue is recrystallized from isopropanol giving 2.96 g of 5-cyano-2,3-dimethoxy-1,4-naphthoquinone, mp 171°-172°.

PREPARATION 9

Di-(2,3-dimethoxy-1,4-naphthoquinone-5)-disulfide (Preparation of Compounds of Formula (XI))

A slurry of potassium thiolacetate (1.5 g, 13.1 mmol) in dimethylformamide (25 ml) is added over 10 minutes to a solution at 0°-5° of 5-amino-2,3-dimethoxy-1,4-naphthoquinone (2.63 g, 10 mmol) in dimethylformamide (25 ml). The mixture is allowed to warm to 22° and, after 2 hours, an additional quantity of potassium thiolacetate (1.25 g) is added. After a further 45 minute reaction, the mixture is added to ice water (500 ml) that was adjusted to pH 6 with acetic acid. The precipitated solid is filtered off, washed with water and recrystallized from chloroform:methanol (1:1) giving 1.32 g. of di(2,3-dimethoxy-1,4-naphthoquinone-5)-disulfide, mp 220°-221°.

PREPARATION 10

2,3-Dimethoxy-5-phenylthio-1,4-naphthoquinone (Preparation of Compounds of Formula (VI) where $R^3$ is phenylthio)

Method A

Sodium nitrite (0.18 g) is added at 0°-5° to a stirred suspension of 5-amino-2,3-dimethoxy-1,4-naphthoquinone (233 mg, 1 mmol) in 0.6 N hydrochloric acid (10 ml) and tetrahydrofuran (1 ml). The mixture is stirred at 5° for 10 minutes until a clear solution is obtained and is then neutralized by the addition of sodium carbonate. The ice cold solution is then slowly added to a vigorously stirred two-phase mixture in a nitrogen atmosphere at 50° composed of potassium hydroxide (0.16 g), water (10 ml), thiophenol (0.32 ml) and ethyl acetate (35 ml). After a total reaction time of 20 min, the mixture is partitioned between ethyl acetate (40 ml) and brine (100 ml). The ethyl acetate phase is dried over MgSO₄ and concentrated in vacuo. The residue is purified by chromatography on a thick layer silica gel plate using acetone:toluene:chloroform (1:20:20) giving a solid that, after recrystallizing from isopropanol, affords 70 mg of 2,3-dimethoxy-5-phenylthio-1,4-naphthoquinone, mp 76°-77°.

Similarly, using imidazolyl-2-thiol in place of thiophenol, 2,3-dimethoxy-5-(imidazol-2-yl)thio-1,4-naphthoquinone, mp 97°-100° C., is prepared.

Method B

Thiophenol (6.0 ml, 59 mmol) is added at −30° to a stirred mixture of 100% sodium hydride (1.4 g, 59 mmol) and dimethylformamide (200 ml) and the resulting mixture is stirred at 22° for 16 hours. This mixture is then cooled to −50° and a solution of di(2,3-dimethoxy-1,4-naphthoquinone-5)-disulfide (13.0 g, 49 mmol) in dimethylformamide (100 ml) is added over 30 min. The resulting mixture is allowed to warm to 22° over 1 hour before being cooled to −50° and neutralized with acetic acid (5.4 ml, 90 mmol). The reaction mixture is then poured into a mixture of water (1.8 l) and methanol (700 ml). The precipitated material is filtered off and recrystallized from methanol giving 10.3 g of 2,3-dimethoxy-5-phenylthio-1,4-naphthoquinone, mp 76°-79°. A further amount (2.2 g) mp 76°-77° is obtained in a second crop from the recrystallization.

Similarly, by substitution of other thiols for thiophenol, $R^1=R^2=OCH_3$, the following compounds are prepared:

2,3-dimethoxy-5-(2-chlorophenylthio)-1,4-naphthoquinone, mp 139°-140°;
2,3-dimethoxy-5-(3-chlorophenylthio)-1,4-naphthoquinone, mp 125°-126°;
2,3-dimethoxy-5-(4-chlorophenylthio)-1,4-naphthoquinone, mp 138°-139°;
2,3-dimethoxy-5-(2,6-dichlorophenylthio)-1,4-naphthoquinone, 14h, mp 158°-159°;
2,3-dimethoxy-5-(4-fluorophenylthio)-1,4-naphthoquinone, mp 124°-125°;
2,3-dimethoxy-5-(2-bromophenylthio)-1,4-naphthoquinone, mp 152°-153°;
2,3-dimethoxy-5-(4-bromophenylthio)-1,4-naphthoquinone, mp 142°-143°;
2,3-dimethoxy-5-(4-methoxyphenylthio)-1,4-naphthoquinone, mp 104°-105°;
2,3-dimethoxy-5-(4-nitrophenylthio)-1,4-naphthoquinone, mp 213°-214°;
2,3-dimethoxy-5-(2-ethylphenylthio)-1,4-naphthoquinone, mp 114°-116°;
2,3-dimethoxy-5-pyridin-2-ylthio-1,4-naphthoquinone, mp 110°-111°;
2,3-dimethoxy-5-pyridin-4-ylthio-1,4-naphthoquinone, mp 158°-159°; and
2,3-dimethoxy-5-(4-acetylaminophenylthio)-1,4-naphthoquinone, mp 118°-127°.

PREPARATION 11

2,3-Dimethoxy-5-methylthio-1,4-naphthoquinone (Preparation of Compounds of Formula (VI) where $R^3$ is methylthio)

Sodium borohydride (100 mg) is added portionwise to a stirred suspension of di(2,3-dimethoxy-1,4-naphthoquinone-5)-disulfide (0.5 g, 1 mmol) in 7:1 tetrahydrofuran:isopropanol (40 ml) in a nitrogen atmosphere until TLC analysis indicates that no starting material remains. Methyl iodide (0.2 ml) is then added and, after 5 minutes, the reaction mixture is poured into ice water (300 ml). 10% Ferric chloride (10 ml) is subsequently added. The precipitated solid is filtered off, washed with water and recrystallized from isopropanol giving 0.36 g of 2,3-dimethoxy-5-methylthio-1,4-naphthoquinone, mp 112°–113°.

By substituting other alkyl iodides for methyl iodide the following are prepared;

2,3-dimethoxy-5-benzylthio-1,4-naphthoquinone, m.p. 142°–143°;

2,3-dimethoxy-5-n-dodecylthio-1,4-naphthoquinone, m.p. 88°–89°; and 2,3-dimethoxy-5-methoxycarbonylmethylthio-1,4-naphthoquinone, m.p. 119°–120°.

PREPARATION 12

2,3-Dimethoxy-5-phenylsulfinyl-1,4-naphthoquinone (Preparation of Compounds of Formula (VI) where $R^3$ is phenylsulfinyl)

Forty percent (w/v) peracetic acid in acetic acid (1 ml) is added over 30 minutes to a solution of 2,3-dimethoxy-5-phenylthio-1,4-naphthoquinone (0.98 g, 3 mmol) in methylene chloride (15 ml). Excess peracetic acid is destroyed by the addition of a few milligrams of 5% palladium on carbon and the mixture filtered through a celite bed. The filtrate is concentrated in vacuo and the residue recrystallized from methanol giving 0.59 g of 2,3-dimethoxy-5-phenylsulfinyl-1,4-naphthoquinone, mp 169°–170° and a second crop of 0.14 g, mp 165°–167°.

Similarly, using either peracetic acid or m-chloroperbenzoic acid, the following compounds are prepared from the respective thio compounds:

2,3-dimethoxy-5-(imidazol-2-yl)sulfinyl-1,4-naphthoquinone, 2,3-dimethoxy-5-(2-chlorophenyl)sulfinyl-1,4-naphthoquinone, mp 193°–194°;

2,3-dimethoxy-5-(3-chlorophenyl)sulfinyl-1,4-naphthoquinone, mp 150°–151°;

2,3-dimethoxy-5-(4-chlorophenyl)sulfinyl-1,4-naphthoquinone, mp 191°–192°;

2,3-dimethoxy-5-(2,6-dichlorophenyl)sulfinyl-1,4-naphthoquinone, mp 210°–211°;

2,3-dimethoxy-5-(4-fluorophenyl)sulfinyl-1,4-naphthoquinone, mp 133°–134°;

2,3-dimethoxy-5-(2-bromophenyl)sulfinyl-1,4-naphthoquinone, 16h, mp 199°–200°;

2,3-dimethoxy-5-(4-bromophenyl)sulfinyl-1,4-naphthoquinone, mp 144°–145°;

2,3-dimethoxy-5-(4-methoxyphenyl)sulfinyl-1,4-naphthoquinone, mp 110°–111°;

2,3-dimethoxy-5-(4-nitrophenyl)sulfinyl-1,4-naphthoquinone, mp 193°–194°;

2,3-dimethoxy-5-(2-ethylphenyl)sulfinyl-1,4-naphthoquinone, mp 166°–167°;

2,3-dimethoxy-5-(pyrimidin-2-yl)sulfinyl-1,4-naphthoquinone, mp 185°–186°;

2,3-dimethoxy-5-(pyrimidin-4-yl)sulfinyl-1,4-naphthoquinone, mp 102°–103°;

2,3-dimethoxy-5-methylsulfinyl-1,4-naphthoquinone, mp 102°–105°;

2,3-dimethoxy-5-benzylsulfinyl-1,4-naphthoquinone, mp 160°–161°;

2,3-dimethoxy-5-n-dodecylsulfinyl-1,4-naphthoquinone, mp 88°–89°; and 2,3-dimethoxy-5-methoxycarbonylmethylsulfinyl-1,4-naphthoquinone, mp 158°–159°.

PREPARATION 13

2,3-Dimethoxy-5-(4-methylpyridiniumthio)-1,4-naphthoquinone methyl sulfate

A mixture of dimethylsulfate (0.19 ml, 2 mmol) and 2,3-dimethoxy-5-(4-methylpyridinylthio)-1,4-naphthoquinone (327 mg, 1 mmol) in tetrahydrofuran (10 ml) is heated under reflux for 3 hours and then cooled to 20°. The orange solid is filtered off, washed with tetrahydrofuran and recrystallized from ethanol:isopropanol giving 279 mg of 2,3-dimethoxy-5-(4-methylpyridiniumthio)-1,4-naphthoquinone methyl sulfate mp 160°–162° and a second crop of 110 mg.

Similarly prepared is 2,3-dimethoxy-5-(2-methylpyridiniumthio)-1,4-naphthoquinone methyl sulfate.

Similarly, the following compounds are prepared by the above method:

2,3-dimethoxy-5-(2-methylpyridiniumsulfinyl)-1,4-naphthoquinone methyl sulfate, m.p. 175°–176°; and 2,3-dimethoxy-5-(4-methylpyridiniumsulfinyl)-1,4-naphthoquinone methyl sulfate, m.p. 175°–176°;

PREPARATION 14

2,3-Dimethoxy-5-phenylsulfonyl-1,4-naphthoquinone (Preparation of Compound of Formula (VI) where $R^3$ is phenylsulfonyl)

A mixture of m-chloroperbenzoic acid (300 mg) and 2,3-dimethoxy-5-phenylthio-1,4-naphthoquinone (200 mg, 0.61 mmol) in methylene chloride (5 ml) is stirred at 22° for 16 hours and the resulting solution then passed through an alumina column (10 g of Activity 1) eluting with chloroform. The eluates are concentrated to dryness and the residue is crystallized from isopropanol giving 95 mg of 2,3-dimethoxy-5-phenylsulfonyl-1,4-naphthoquinone, mp 141°–142°.

PREPARATION 15

2,3-Dihydroxy-5-phenylthio-1,4-naphthoquinone (Preparation of Compounds of Formula (VI) where $R^1 = R^2 = OH$)

A solution of 2,3-dimethoxy-5-phenylthio-1,4-naphthoquinone (3 g, 9.2 mmol) in methylene chloride is added dropwise over 20 minutes at −65° to a stirred solution of freshly distilled boron trichloride (10 ml) in methylene chloride (100 ml). After a further 5 minute reaction, 1:1 chloroform:methanol (20 ml) is added and the resulting solution is concentrated to dryness in vacuo. The residue is recrystallized from 2:1 methanol:water (150 ml) and then isopropanol giving 2.0 g of 2,3-dihydroxy-5-phenylthio-1,4-naphthoquinone, mp 228°–230°.

In a similar manner, substituting the appropriate substituted 2,3-dialkoxy-1,4-naphthoquinone for 2,3-dimethoxy-5-phenylthio-1,4-naphthoquinone, the following compounds are prepared:

5-chloro-2,3-dihydroxy-1,4-naphthoquinone, mp 240°–245°.

6-chloro-2,3-dihydroxy-1,4-naphthoquinone, 2- or 3-hydroxy-2- or 3-methoxy-5-cyano-1,4-naphthoquinone, mp 237°–242°, 5-bromo-2,3-dihydroxy-1,4-naphthoquinone, 6-bromo-2,3-dihydroxy-1,4-naphthoquinone, 6-methoxy-2,3-dihydroxy-1,4-naphthoquinone, and 2- or 3-hydroxy-2- or 3-methoxy-5-phenylsulfinyl-1,4-naphthoquinone, mp 215°–220°.

PREPARATION 16

2,3-Dibenzyloxy-5-cyano-1,4-naphthoquinone

5-Cyano-2,3-dimethoxy-1,4-naphthoquinone (972 mg, 4 mmol) is dissolved in tetrahydrofuran (100 ml) containing benzyl alcohol (8 ml) and the tetrahydrofuran (40 ml) is distilled off. The remaining solution is cooled to 15° and sodium hydride (5 mg) with 3 Å molecular sieve (2 g) is added. The resulting mixture is stirred at 15°-20° for 20 minutes. The mixture is filtered through a celite bed, the filtrate concentrated to dryness and the residue crystallized from isopropanol giving 1.01 g of 2,3-dibenzyloxy-5-cyano-1,4-naphthoquinone, mp 118°-121°.

Treatment of 2,3-dibenzyloxy-5-cyano-1,4-naphthoquinone with boron trichloride as in Preparation 15 above gives 2,3-dihydroxy-5-cyano-1,4-naphthoquinone, mp 305°-312°.

EXAMPLE 1

6-Chloro-2,2,3,3-tetrahydroxy-1,2,3,4-tetrahydro-1,4-naphthoquinone (Compounds of formula (I))

Chlorine gas is passed through a stirred suspension of 6-chloro-2,3-dihydroxy-1,4-naphthoquinone (225 mg. 1 mmol) in 50% acetic acid (2 ml) until a pale yellow clear solution is obtained. Excess chlorine is then removed by a nitrogen stream. The resulting solution is concentrated to dryness in vacuo and the residue recrystallized from acetonitrile:benzene (1:2) giving 214 mg of 6-chloro-2,2,3,3-tetrahydroxy-1,2,3,4-tetrahydro-1,4-naphthoquinone as a white crystalline solid with mp 134°-136°.

In a similar manner, the following compounds are prepared:

6-fluoro-2,2,3,3-tetrahydroxy-1,2,3,4-tetrahydro-1,4-naphthoquinone, mp 131°-132°;
6-bromo-2,2,3,3-tetrahydroxy-1,2,3,4-tetrahydro-1,4-naphthoquinone, mp 147°-148°;
6-methoxy-2,2,3,3-tetrahydroxy-1,2,3,4-tetrahydro-1,4-naphthoquinone, mp 130°-131°;
6-cyano-2,2,3,3-tetrahydroxy-1,2,3,4-tetrahydro-1,4-naphthoquinone;
5-chloro-2,2,3,3-tetrahydroxy-1,2,3,4-tetrahydro-1,4-naphthoquinone;
5-cyano-2,2,3,3-tetrahydroxy-1,2,3,4-tetrahydro-1,4-naphthoquinone;
5-methoxycarbonylmethylthio-2,2,3,3-tetrahydroxy-1,2,3,4-tetraydro-1,4-naphthoquinone;
5-phenylthio-2,2,3,3-tetrahydroxy-1,2,3,4-tetrahydro-1,4-naphthoquinone;
5-(imidazol-2-ylthio)-2,2,3,3-tetrahydroxy-1,2,3,4-tetrahydro-1,4-naphthoquinone;
5-(2-chlorophenylthio)-2,2,3,3-tetrahydroxy-1,2,3,4-tetrahydro-1,4-naphthoquinone;
5-(4-chlorophenylthio)-2,2,3,3-tetrahydroxy-1,2,3,4-tetrahydro-1,4-naphthoquinone;
5-(2,6-dichlorophenylthio)-2,2,3,3-tetrahydroxy-1,2,3,4-tetrahydro-1,4-naphthoquinone;
5-(4-fluorophenylthio)-2,2,3,3-tetrahydroxy-1,2,3,4-tetrahydro-1,4-naphthoquinone;
5-(4-bromophenylthio)-2,2,3,3-tetrahydroxy-1,2,3,4-tetrahydro-1,4-naphthoquinone;
5-(4-methoxyphenylthio)-2,2,3,3-tetrahydroxy-1,2,3,4-tetrahydro-1,4-naphthoquinone;
5-(4-nitrophenylthio)-2,2,3,3-tetrahydroxy-1,2,3,4-tetrahydro-1,4-naphthoquinone;
5-(2-ethylphenylthio)-2,2,3,3-tetrahydroxy-1,2,3,4-tetrahydro-1,4-naphthoquinone;
5-(pyridin-2-ylthio)-2,2,3,3-tetrahydroxy-1,2,3,4-tetrahydro-1,4-naphthoquinone;
5-(pyridin-4-ylthio)-2,2,3,3-tetrahydroxy-1,2,3,4-tetrahydro-1,4-naphthoquinone;
5-(4-acetylaminophenylthio)-2,2,3,3-tetrahydroxy-1,2,3,4-tetrahydro-1,4-naphthoquinone;
5-methylthio-2,2,3,3-tetrahydroxy-1,2,3,4-tetrahydro-1,4-naphthoquinone;
5-phenylsulfinyl-2,2,3,3-tetrahydroxy-1,2,3,4-tetrahydro-1,4-naphthoquinone;
5-(2-chlorophenyl)sulfinyl-2,2,3,3-tetrahydroxy-1,2,3,4-tetrahydro-1,4-naphthoquinone;
5-(4-methoxyphenyl)sulfinyl-2,2,3,3-tetrahydroxy-1,2,3,4-tetrahydro-1,4-naphthoquinone;
5-(pyrimidin-2-yl)sulfinyl-2,2,3,3-tetrahydroxy-1,2,3,4-tetrahydro-1,4-naphthoquinone;
5-methylsulfinyl-2,2,3,3-tetrahydroxy-1,2,3,4-tetrahydro-1,4-naphthoquinone;
5-n-dodecylsulfinyl-2,2,3,3-tetrahydroxy-1,2,3,4-tetrahydro-1,4-naphthoquinone; and
5-phenylsulfonyl-2,2,3,3-tetrahydroxy-1,2,3,4-tetrahydro-1,4-naphthoquinone.

What is claimed is:

1. A pharmaceutical composition in a form suitable for topical administration to mammals which comprises a pharmaceutically acceptable, non-toxic carrier and a psoriasis-relieving amount of a compound represented by the formula

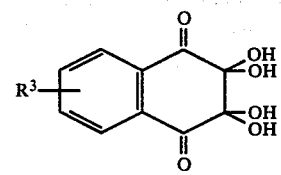

wherein
$R^3$ is selected from the group consisting of halo, cyano, alkoxy of one to eighteen carbon atoms and $-S(O)_nR$
wherein
n is 0, 1 or 2; and
R is selected from the group consisting of alkoxycarbonyl-alkyl wherein alkoxy contains one to four carbon atoms and the alkyl chain contains one to eighteen carbon atoms; alkyl of one to eighteen carbon atoms; phenylalkyl wherein the alkyl group contains one to eighteen carbon atoms and the phenyl ring is optionally substituted by one or more lower alkyl of one to four carbon atoms, lower alkoxy of one to four carbon atoms, halo or lower acyl of two to seven carbon atoms; phenyl optionally substituted by one or more halo, cyano, nitro, amino, acylamino of two to five carbon atoms, lower alkoxy of one to four carbon atoms or lower alkyl of one to four carbon atoms; and heterocyclic aryl or the pharmaceutically acceptable salt thereof, said aryl having 3 to 9 ring carbon atoms and having in the ring one or two heteroatoms selected from the group consisting of nitrogen, oxygen and sulfur.

2. The composition of claim 1 wherein $R^3$ is selected from the group consisting of halo, cyano, phenylthio, methylthio, and alkoxy.

3. The composition of claim 2 wherein said compound is represented by the formula

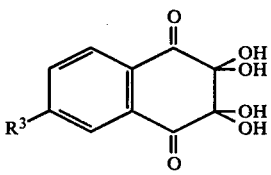

wherein R³ is as defined in claim 2.

4. The composition of claim 3 wherein R³ is chloro.
5. The composition of claim 3 wherein R³ is bromo.
6. A method for relieving the condition of psoriasis in a mammal which comprises topically administering to said mammal a psoriasis-relieving amount of a compound represented by the formula

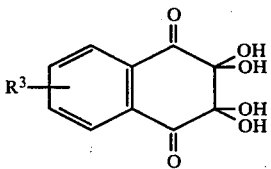

wherein
R³ is selected from the group consisting of halo, cyano, alkoxy of one to eighteen carbon atoms and —S(O)ₙR wherein
n is 0, 1 or 2; and
R is selected from the group consisting of alkoxycarbonyl-alkyl wherein the alkoxy contains one to four carbon atoms and the alkyl chain contains one to eighteen carbon atoms; alkyl of one to eighteen carbon atoms; phenylalkyl wherein the alkyl group contains one to eighteen carbon atoms and the phenyl ring is optionally substituted by one or more lower alkyl of one to four carbon atoms, lower alkoxy of one to four carbon atoms, halo or lower acyl of two to seven carbon atoms; phenyl optionally substituted by one or more halo, cyano, nitro, amino, acylamino of two to five carbon atoms, lower alkoxy of one to four carbon atoms or lower alkyl of one to four carbon atoms; and heterocyclic aryl or the pharmaceutically acceptable salt thereof, said aryl having 3 to 9 ring carbon atoms and having in the ring one or two heteroatoms selected from the group consisting of nitrogen, oxygen and sulfur.

7. The method of claim 6 wherein R³ is selected from the group consisting of halo, cyano, phenylthio, methylthio, and alkoxy.

8. The method of claim 7 wherein said compound is represented by the formula

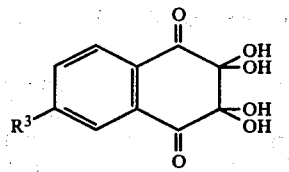

and R³ is as defined in claim 7.

9. The method of claim 8 wherein R³ is chloro.
10. The method of claim 8 wherein R³ is bromo.

* * * * *